United States Patent [19]

Au-Yang

[11] Patent Number: 5,257,545
[45] Date of Patent: Nov. 2, 1993

[54] METHOD AND APPARATUS TO MONITOR CHECK VALVES

[75] Inventor: Man K. Au-Yang, Lynchburg, Va.

[73] Assignee: B&W Nuclear Service Company, Lynchburg, Va.

[21] Appl. No.: 790,732

[22] Filed: Nov. 8, 1991

Related U.S. Application Data

[63] Continuation-in-part of Ser. No. 622,903, Dec. 6, 1990, abandoned.

[51] Int. Cl.⁵ .................... G01N 29/10; G01N 29/24
[52] U.S. Cl. ........................................ 73/597; 73/168; 367/99; 376/248; 376/252
[58] Field of Search ...................... 73/597, 168, 119 A, 73/587, 572, 627, 629; 137/554; 367/99; 376/245, 252

[56] References Cited

U.S. PATENT DOCUMENTS

| | | | |
|---|---|---|---|
| 4,782,702 | 11/1988 | Boone et al. | 73/597 |
| 4,833,453 | 5/1989 | Twerdochlib | 73/587 |
| 4,920,802 | 5/1990 | McMullin et al. | 73/597 |
| 4,977,778 | 12/1990 | Nafziger et al. | 73/597 |
| 5,008,841 | 4/1991 | McElroy | 73/587 |
| 5,154,080 | 10/1992 | Hill et al. | 73/597 |
| 5,159,835 | 11/1992 | Nafziger et al. | 73/594 |

Primary Examiner—Hezron E. Williams
Assistant Examiner—Rose M. Finley
Attorney, Agent, or Firm—Vytas R. Matas; R. J. Edwards

[57] ABSTRACT

A non-intrusive vibration measurement system and method using commercial ultrasonic instruments together with digital signal filtering and analysis techniques is adapted to quantitatively detect vibrations as small as 0.04-inch peak-to-peak. The system and its methodology is used for in-service vibration monitoring of internal components of check valves, pumps, nuclear reactors, steam generators and heat exchangers, especially when the vibration frequency is too low for quantitative analysis by accelerometers and when the strain induced is too low for strain gauge analysis, and when the vibrating component is in an "encased" environment.

16 Claims, 7 Drawing Sheets

METHOD AND APPARATUS TO MONITOR CHECK VALVES

This is a continuation-in-part of U.S. application Ser. No. 07/622,903 filed Dec. 6, 1990, now abandoned entitled "Method and Apparatus to Monitor Check Valves" by Altona, et al.

BACKGROUND OF THE INVENTION

1. Field of the Invention

The present invention generally relates to methods and apparatus for ultrasonically sensing vibrations and particularly to a method and apparatus for non-intrusively measuring low frequency vibrations using ultrasonic techniques.

2. Description of the Prior Art

The importance of quantitatively determining the vibration frequencies and amplitudes of structural systems and components is well known, both in the laboratory as a research tool and in the field as a monitoring and diagnostic technique. Of all the vibration-measuring instruments in existence, the accelerometer is the most commonly used because of its ease in application, ruggedness and economy. Nevertheless, the accelerometer has its limitations. Its sensitivity decreases with frequency and this sensor is not very useful when the frequency of vibration is below a few cycles per second. In addition, to be effective, the accelerometer must be mounted directly on the vibrating surface. Thus, it cannot be used, for example, to quantitatively measure the vibration of a pivoted valve disc inside a check valve, without disassembling the check valve. Further, it cannot be used to measure the vibration of very slender structures such as reactor control rods, because of their lower natural frequencies of vibration.

Strain gauges are also used, but again they must be mounted directly onto the vibrating surface and are thus again an "intrusive" vibration sensor. Furthermore, the strain gauge will not work if the vibration does not produce any strain, such as is the case in trying to determine the flutter of a pivoted valve disc in a check valve.

Displacement probes include both contacting and non-contacting types. They are another commonly used vibration sensor. The displacement probe needs a sturdy mounting surface close to the vibrating surface and measures the relative motion between these two surfaces. As such it is usually an "intrusive" vibration sensor. It is more difficult to install properly compared with the accelerometer; however, it does work even at very low frequencies and when the vibration does not produce any strain.

The dynamic pressure transducer is a very sensitive instrument used to measure pressure fluctuations in fluids. They can also be used indirectly to measure the vibrations of structures immersed in fluids, because a vibrating structure induces pressure fluctuations in the surrounding fluid. However, to mount pressure transducers, tap holes must often be drilled through the pressure boundary, again making the dynamic pressure transducer an "intrusive" instrument. In addition, dynamics pressure transducers are extremely fragile and deducing structural vibration amplitudes from the measured pressure fluctuation often requires sophisticated analysis.

Low frequency vibrations with fairly large amplitudes can often be visually "measured" either with the naked eye or with the aid of high-speed photography. This technique, however, requires the vibrating component to be accessible and visible and would again be "intrusive".

In view of the foregoing description of the present state of the art, it will be seen that none of the prior art devices provided a non-intrusive device that could monitor low frequency vibrations of encased or non-accessible elements let alone provide quantitative measurements of such vibrations.

SUMMARY OF THE INVENTION

The present invention solves all the problems associated with prior art devices, as well as others, by providing a non-intrusive accurate monitor for quantitatively monitoring internal moving parts of devices such as power plant components using available ultrasonic instruments in conjunction with known modern, high speed-digital filtering and signal analysis techniques. Because of the non-intrusive nature of the present invention, its use is ideally suitable for applications to in-service monitoring and diagnosis of components found in the power generation, process and petrochemical industries, such as pumps, valves, heat exchangers, steam generators and nuclear reactor internals. The present invention can also be used in the laboratory as an alternative to the accelerometer when, for example, the anticipated vibration frequency of the measured device is very low. Usually the system of the present invention allows the use of off-the-shelf, commercial ultrasonic equipment for most applications. Occasionally, simple modifications may be necessary for particular applications. An example of this application involves the use of the system as a detector for non-intrusively monitoring check valve internal components. This application requires that (1) the vibrating component of the check valve be immersed in an ultrasonic conducting fluid such as water and (2) the valve disc flutter frequency must not be higher than a few hundred cycles per second (Hz).

Thus it will be seen that one aspect of the present invention is to provide a non-intrusive, low frequency, vibration detector for non-accessible internal components vibrating within a device enclosing this component.

Another aspect of the present invention is to provide an ultrasonic device to quantitatively measure the flutter of check valve discs.

Yet another aspect of the present invention is to provide a digitally filtered output of an ultrasonic detector to provide a display of discriminated low frequency vibration which was sensed by the detector and from which a quantitative analysis of amplitude and frequency may be made.

Still another aspect of the present invention is to provide a monitoring device having a combination ultrasonic detector and acoustic detector to monitor the internal condition of a check valve.

These and other aspects of the present invention will be more fully understood from a consideration of the following description of the preferred embodiment when considered along with the accompanying drawings.

BRIEF DESCRIPTION OF THE DRAWINGS

FIG. 5 depicts the (a) raw data from the ultrasonic transducer and instrument sensing the check valve as shown in FIG. 1;

DESCRIPTION OF THE PREFERRED EMBODIMENT

Figure 1:
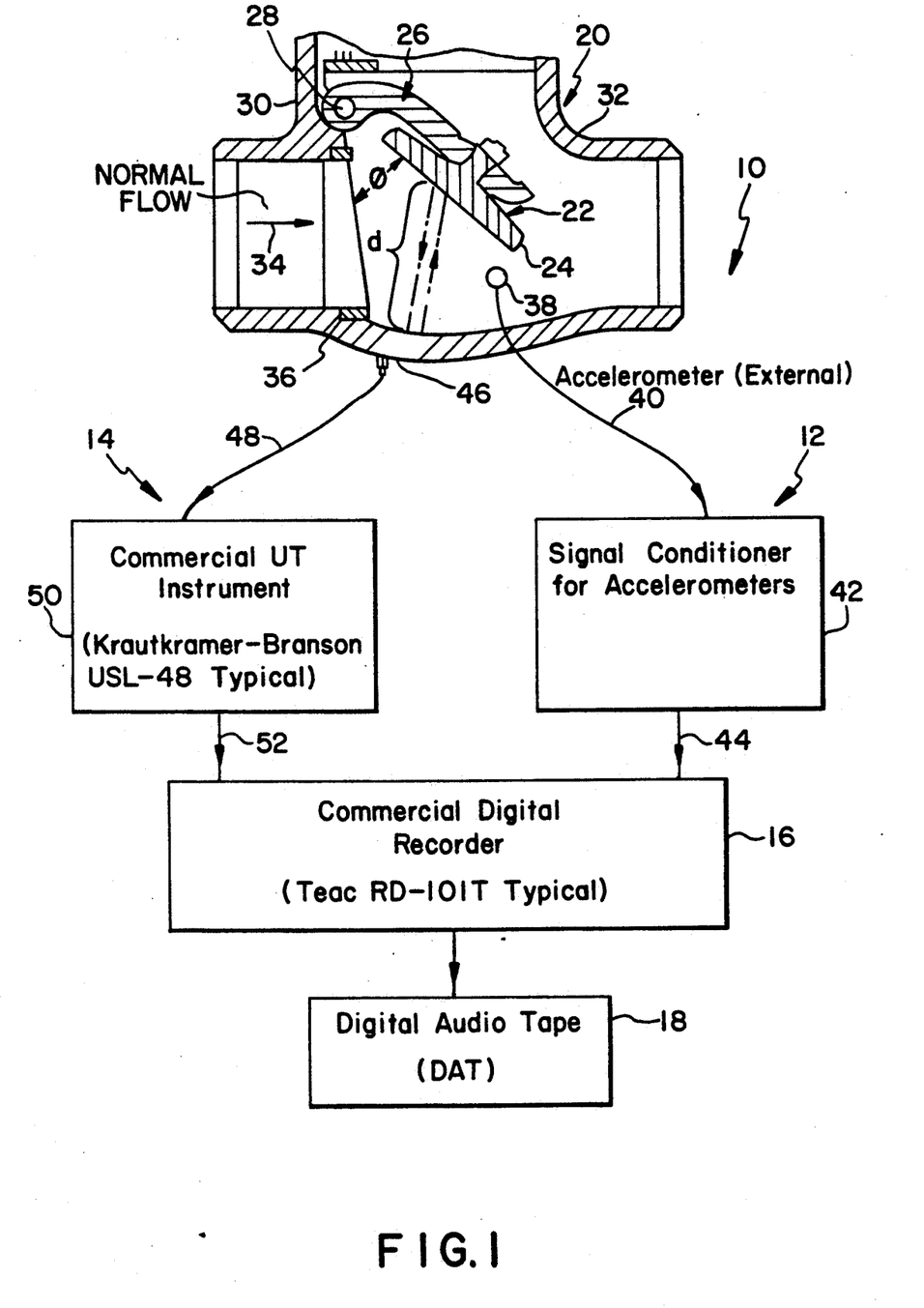
FIG. 1 is a schematic showing a check valve monitor having a combination of ultrasonic instruments and accelerometers to monitor the internal condition of a check valve.

Referring now to the drawings wherein the showings are for purposes of describing a preferred embodiment of the present invention and are not intended to limit the invention thereto, FIG. 1 shows a check valve monitoring system (10) comprising an acoustic system (12) and an ultrasonic system (14). Signals from both the acoustic (12) as well as the ultrasonic system (14) are sent to a known commercial digital recorder (16) which records these signals onto a digital audio tape (18).

As is best seen in FIG. 1, a check valve (20) is positioned in line with a conduit (not shown) for conducting fluid flow through the check valve. The principle moving part of the check valve (20) is the disc assembly (22) which comprises a disc element (24) connected to an arm (26) which is pivotable by virtue of a hinge pin (28) mounted to the body (30) of the check valve (20). The check valve (20) includes a back stop (32) for holding the disc assembly (22) against the body (30) of the check valve (20) to maintain the check valve (20) in the full open position which allows the flow of fluid, such as water, through the check valve (20) in the direction shown by the arrow (34). The check valve (20) also has a closed position wherein the arm (26) is pivoted to have the disc element (24) sealed against a valve seat (36) to shut-off the flow of water through the check valve.

The acoustic system (12) is comprised of an accelerometer (38) mounted on the outside body (30) of the check valve (20) by any suitable means such as adhesive, strapping, or a magnetic mount. Although only one accelerometer (38) is shown for ease of illustration, it will be understood that two or more accelerometers (38) may be spacedly mounted on the body (30) in other embodiments of this invention.

The accelerometer (38) is a passive listening device that qualitatively detects audible sounds generated within the check valve (20) such as fluid flow, the tapping of the disc (24) against the valve seat (36) or the arm (26) against the backstop (32). Also, sounds generated by a loose or worn hinge pin (28) may be detected by the accelerometer (38). These sounds detected by the accelerometer (38) are sent along conductive cable or line (40) to a signal conditioner (42). The signal conditioner (42) converts these acoustic signals to electrical signals which are filtered and amplified and sent along conductor (44) to a known commercial digital recorder (16) such as the Teac RD-101T. The recorder (16) records the signals in-situ on a digital audio tape (18) (DAT) which tape may be then taken to another ex-situ location for analysis as will be described later. Of course, the analysis may also be done in-situ.

The ultrasonic system (14) is comprised of a known ultrasonic transducer (46) mounted on the outside of body (30) of the check valve (20) by any suitable means such as adhesive, magnetic mounting, being strapped around the check valve (20) or even being hand-held against the check valve body (20). The ultrasonic transducer (46) is connected by way of a conductive cable (48) to a commercially available ultrasonic instrument (50), such as the Krautkramer-Branson Model USL-48, Portable Ultrasonic Flaw Detector and Thickness Tester. This instrument (50) is in turn connected by a conductive cable (52) to the commercial digital recorder (16) which is able to record the signals from the ultrasonic instrument (50) either independently or in conjunction with the signals from the accelerometer (42) and in turn record either of the mentioned signals on the digital audio tape (18) in a manner well known to those skilled in this art.

In normal operation, the function of the ultrasonic instrument (50) is to determine the ultrasonic transit time between the ultrasonic transducer (46) and a discontinuity in the medium through which the ultrasonic wave propagated by the transducer (46) passes. In the present application, the ultrasonic transducer (46) passes ultrasonic waves through the water present in the check valve (20) to the disc (24) from which it is reflected back to the transducer (46). The ultrasonic transducer (46) in this application acts both as an ultrasonic generator and a receiver, although two dedicated transducers one for generating and the other for receiving can also be used.

The instrument (50) first generates a series of high-voltage excitation pulses to apply to the transducer (46). The transducer (46) converts these pulses into ultrasonic waves which are aimed at the disc (24). At the same instant that the instrument (50) generates the pulses, timing circuitry within the instrument (50) begins a counting sequence. When the sound wave generated by the transducer (46) impinges upon the disc (24) and is reflected therefrom, as may be seen by the dotted arrows in FIG. 1, the reflected wave is picked up by the transducer (46) which is now in a passive "listening" mode. The transducer (46) is controlled by the instrument (50) to alternate between the generating and receiving mode. Since the time difference between generated pulses is much larger than the time required for the waves generated by the transducer (46) to be passed through the water and reflected back by the member (24). The generator (46) is easily switched between active and passive to accommodate both the generation and reception of ultrasonic waves.

The timing circuitry (not shown) of the instrument (50) is actuated by the transducer (46) to shut-off and determine the elapsed time for the ultrasonic waves to be passed through the water upon receipt of the reflected wave from the member (24), in a known manner, and this time interval is recorded on the digital audio tape (18). This is done by recording the peak voltages which are proportional to the lapsed time between the emission and reception of the ultrasonic pulses send and received by the transducer (46). Knowing the speed of sound in water at the specific water pressure and temperature, a computation is made of the distance of the discontinuity (the disc/water boundary from the transducer). Thus, it will be seen that the ultrasonic transducer (46) and the instrument (50), which includes microprocessor capability, may be programmed in a known manner to determine the position of the disc (24) within the check valve body (20).

The qualitative detection of large amplitude flutter of the disc (24) within the check valve (20) is also detectable by the method and apparatus disclosed. However, the device and methods are further adapted to quantitatively measure small amplitude vibrations of the disc (24). Such quantitative measurements are only possible when the ultrasonic instrument (50) is used in conjunction with known high-speed digital signal analysis techniques. Also certain preliminary requirements must first be met to allow the use of the ultrasonic instrument (50) as a quantitative vibration measuring device.

First, the frequency of the ultrasonic signal must be chosen so that its wavelength in the conducting medium (water) is smaller than the estimated peak-to-peak vibration amplitude to be measured. Thus, if a 2.0 MHz ultrasonic signal is used and a conducting medium is water at room temperature in which the velocity of sound is approximately 5,000 feet per second, the wavelength of the ultrasonic signal is about 0.03 inch. A vibration amplitude much smaller than 0.03 inch peak-to-peak cannot be accurately measured, although it still can be qualitatively detected.

Secondly, the ultrasonic transmitter-receiver (46) must be mounted on the body (30) of the check valve (20) so that the round trip travel time for the transmitted and reflected wave is less than the anticipated period of vibration.

Thirdly, the pulse rate must be at least two times higher than the maximum vibration frequency, with a minimum of three times being recommended. Since most commercial ultrasonic detectors have a pulse rate no higher than 1,000 per second, the ultrasonic vibration sensor is essentially a low frequency device applicable to vibrations below 400 Hz unless special ultrasonic instruments are developed especially for these purposes.

Fourthly, digital signal analysis with digital filtering techniques and software are to be written in double precision arithmetics with a microprocessor or a computer (PC) with high resolution screen (not shown) being required to process and display the ultrasonic data. Analog signal analysis techniques with the ultrasonic signals being displayed on an oscilloscope do not have sufficient resolution to quantitatively measure the small amplitude vibrations.

The accelerometer (38) is used to measure high frequency rattling and impact noise generated within the check valve (20) which noises are transmitted to the housing on which the accelerometer (38) is mounted. The position and vibration frequencies and amplitudes of the valve disc (24) are determined by the ultrasonic transducer (46) externally mounted on the check valve (20) body. Thus the ultrasonic system (14) of the combined system can quantitatively measure the position of the valve disc (24) as it opens and closes in addition to being able to measure the vibration frequency and amplitude of the disc (24) as small as 0.03 inches. Further, the ultrasonic system (14) can be used to detect light to moderate cavitation during flow through the check valve (20). The acoustic system (12) of the combined system can qualitatively detect defects in the check valve, flutter of the disc and rattle against the backstop (32) and seal (36) as well as pivot (28) rattle.

Since the signals generated by the ultrasonic system (14) are in the form of discrete time series, they are most easily analyzed directly utilizing modern digital techniques either on-line or off-line. Since the locations of the check valves (20) are often difficult to get to, signals in-situ recorded on the digital audio tape (18) are then taken back to the laboratory or work station for analysis on high resolution screens of microprocessors or microcomputers (PC's). As will be best seen with reference to FIG. 2, the data from the digital audio tape (18) which is digitally recorded on the tapes may require cross-correlation analysis if the channels of data from the acoustic (12) and the ultrasonic (14) instruments were recorded simultaneously or individual analysis if the recording was from one channel. Because of the wide dynamic range offered by digital recorders, virtually no signal conditioning other than what is contained in the ultrasonic instrument (50) and the digital recorder (16) is necessary. The digital filter subroutine (54) eliminates any noise that may have survived to contaminate the data. Any noise that may contaminate the ultrasonic data signal can be filtered off digitally in the analysis stage.

Figure 2:
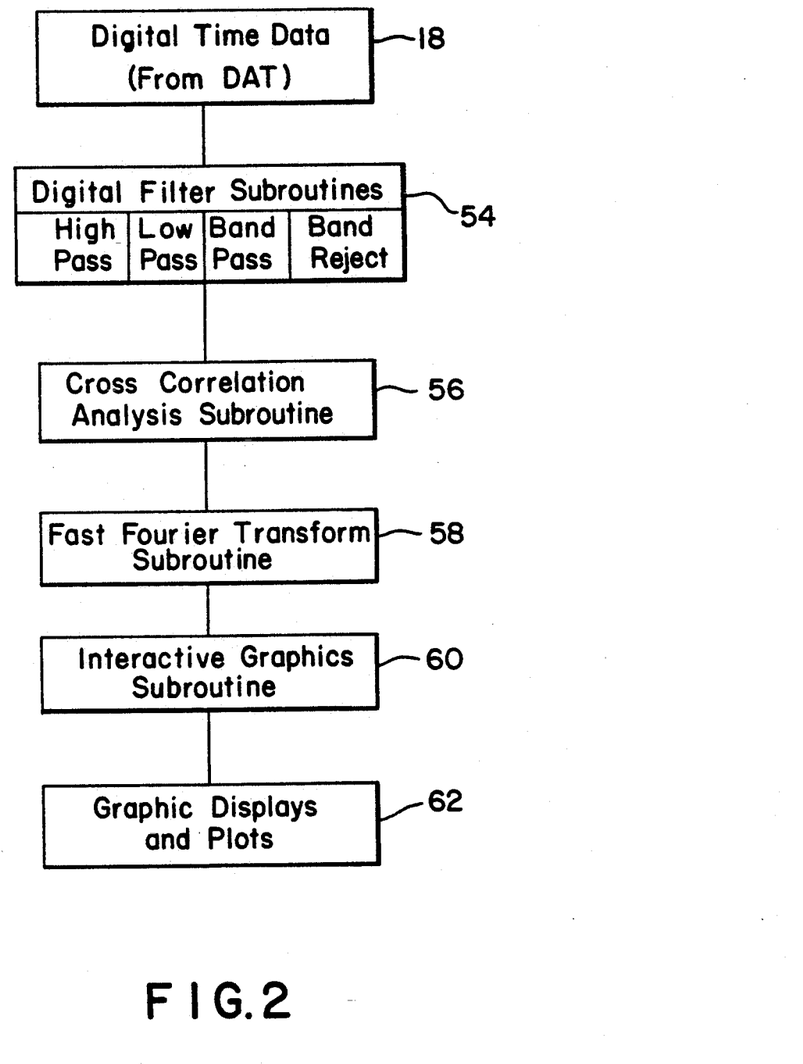
FIG. 2 is a flow chart of a typical digital filtering and signal analysis computer program.

FIG. 2 shows the flow chart of typical digital signal analysis software for the ultrasonic data known to those skilled in the art. The digital data (18) is passed through the digital filter subroutines (54) which utilizes high pass, low pass, band pass and band reject filtering. As was indicated earlier, cross-correlation between the acoustic (12) and the ultrasonic signals or between two acoustic signals is possible. The filtered data is then passed through the cross-correlation analysis subroutine (56). The data next is passed through a fast Fourier Transform transform subroutine (58) that enables the performing of spectral (frequency) analysis of the data. Finally, the interactive graphic subroutine (60) enables the operator to zoom into and enlarge for display (62) local areas of the digitally filtered data from which display (62) the vibration amplitudes and frequencies can be quantitatively determined as will be seen in the following figures.

Figure 3:
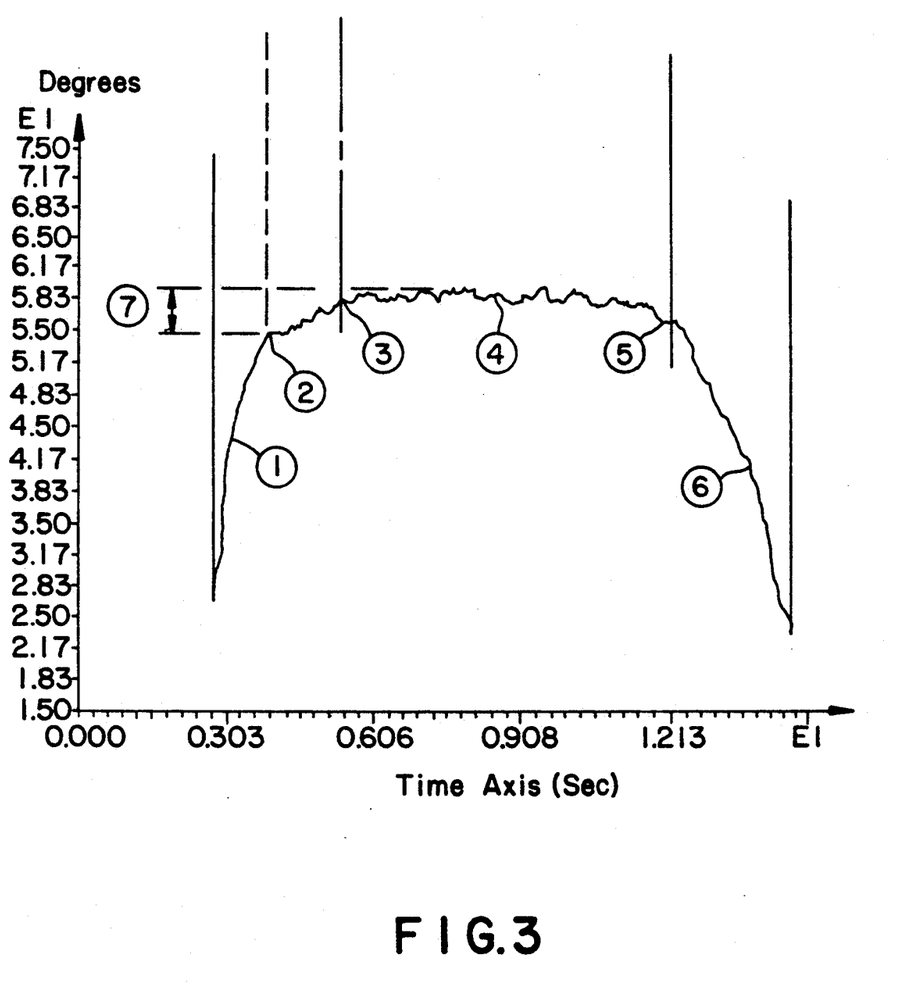
FIG. 3 is a time history of a typical check valve operating cycle as sensed and displayed by the ultrasonic detector of FIG. 1 and filtered and displayed by the software of FIG. 2 showing: (1) disc opening; (2) the disc arm hitting the valve backstop; (3) disc and arm locked against the backstop; (4) check valve fully opened; (5) disc and arm unlocked from the backstop; (6) disc closing the check valve; (7) play between the arm and the disc in the valve open position.

Referring now to FIG. 3, it will be seen that the ultrasonic detector (14) along with the digital filtering technique of FIG. 2 is further software programmed in a known manner to provide display (62) of the time history trace of the disc opening angle. This is done by relating the distance measurement (d) to the angle $\phi$ between the fully closed and fully opened position of the valve (20) as the disc (24) rotates at pivot (28) from its position along seat (36) to its position facing backstop (32). This particular display was for a 12 inch check valve located in a water filtration plant. The display clearly shows that the disc opening along point 1, that the disc arm hit the backstop at point 2 as seen by the flat line extending therefrom, that the disc arm locked along point 3, and that the disc was full open along point 4 as seen by the maximum angle deflection of the arm (26). Point 5 shows the disc assembly being finally set against the backstop (32) while point 6 shows that the disc is closing due to the angular decrease of arm (26), point 7 shows the play between the arm (26) and the disc (24) due to wear between these two moving parts at the pin connection.

Figure 4:
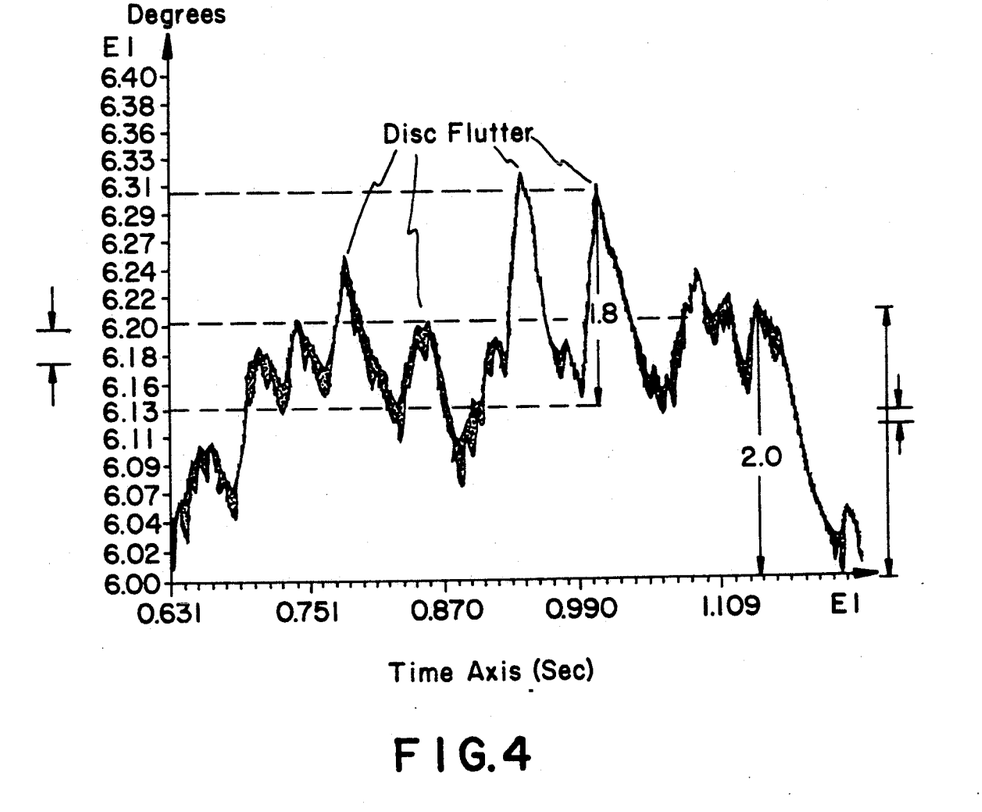
FIG. 4 is a zoom-in of the steady-state portion of the display shown in FIG. 3 showing disc vibration at fully opened position (7).

FIG. 4 shows the graph of the time period shown as 4 in FIG. 3 during which the disc (24) was at its maximum opening position. FIG. 4 shows this maximum opening position zoomed in utilizing the interactive graphic subroutine (60) as is known to those skilled in the art. It will be noted that both FIG. 3 and FIG. 4 have the vertical axis as E1 or 10 times the actual reading. FIG. 4 now displays the disc vibration frequency and amplitude a quantitative measurement may be made. FIG. 4 shows that in this particular case a vibration amplitude in the range of 0.2° can be easily measured by the ultrasonic instrument (50) when utilized in conjunction with the known digital filtering techniques and interactive graphics (60). Since the disc diameter measured was approximately 12 inches, this translates into a peak-to-peak vibration amplitude of about 0.04 inches as determined by the equation (sin $0.2° \times 12$ in.)=0.04 in.

Figure 5A:
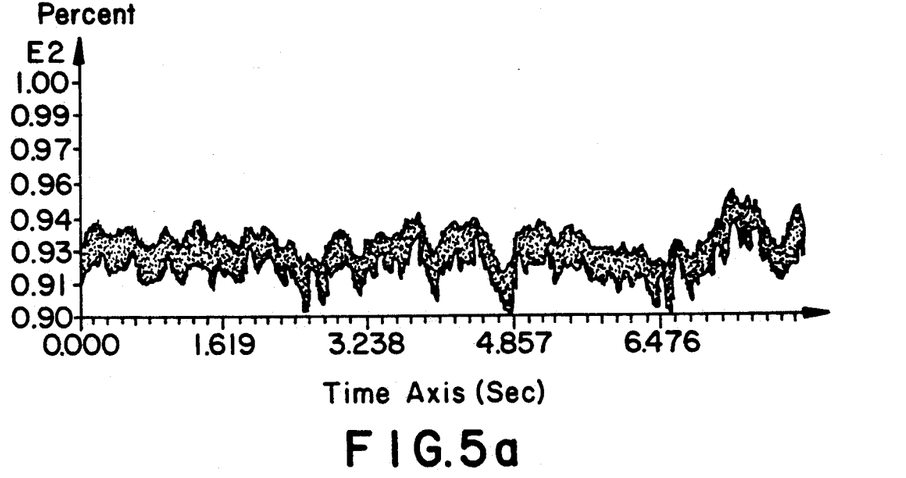
Figure 5B:
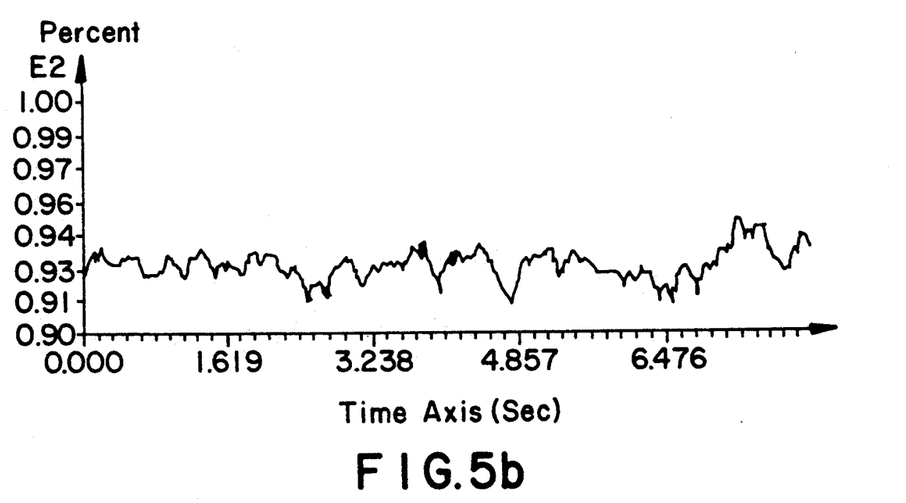
FIG. 5(b) depicts the FIG. 5(a) data after it has been low-pass filtered at 100 Hz by the digital filter of FIG. 2.

Turning next to FIG. 5, it can be seen that the digital filtering technique of FIG. 2 will clean up the "raw" ultrasonic data of FIG. 5(a). As seen in FIG. 5(b), it can be seen that the noise above 100 Hz was eliminated by the low pass digital filter. The filtered signal is thus clean and permits the vibration amplitude to be quantitatively determined as was discussed with reference to FIGS. 3 and 4.

Figure 6:
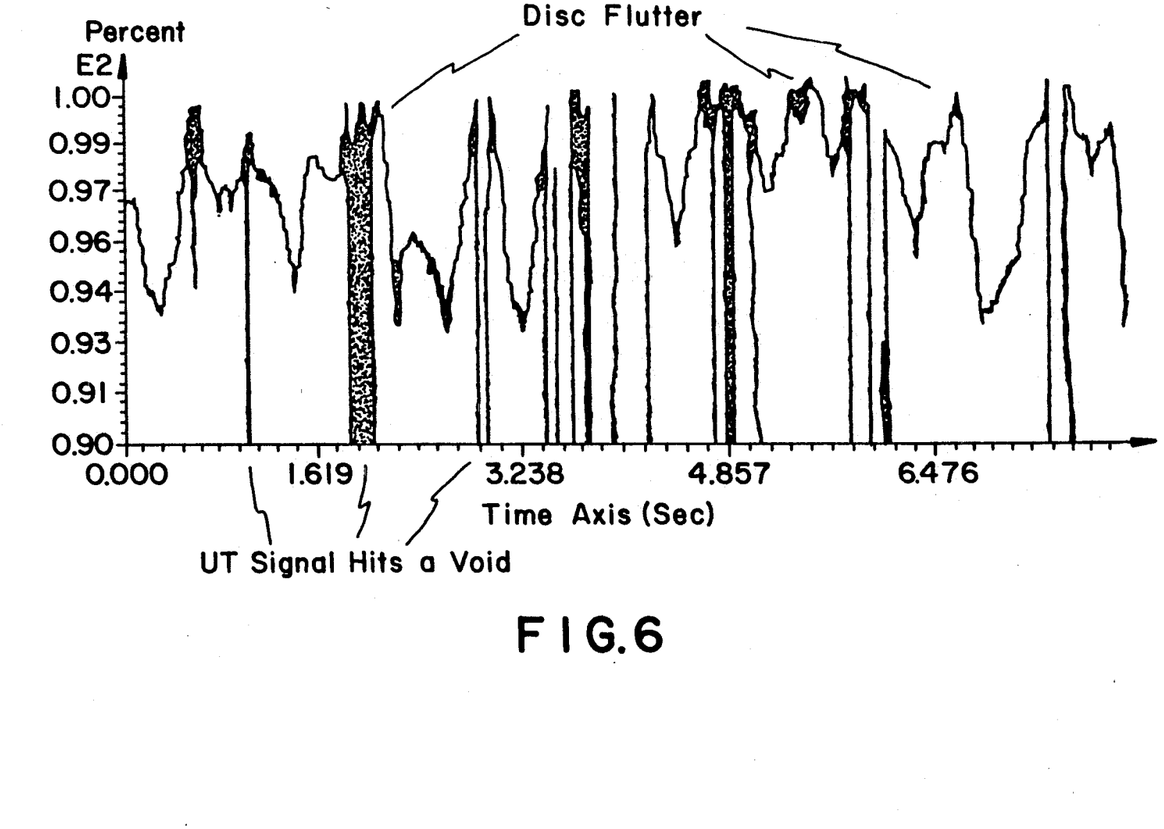
FIG. 6 depicts the time history output of the FIG. 1 and FIG. 2 system monitoring the check valve disc when it is vibrating in lightly cavitating water flow.

Turning now to FIG. 6, it will be seen that the cavitation in the check valve during a flow condition may be measured by the ultrasonic device (14) utilizing these same formentioned techniques. Since there is no reflected signal whenever the ultrasonic wave hits a vapor void in the fluid medium through which it propagates a straight vertical line appears in the time history indicative of cavitation as may be seen in the vertical lines of FIG. 6. Thus from the frequency of occurrence of these vertical lines, a semi-quantitative assessment of the severity of cavitation within the check valve (20) can be made.

There are many other applications for this ultrasonic non-intrusive vibration sensing system in addition to the specifically described preferred embodiment. This ultrasonic system is applicable anywhere where the vibrating component is immersed in an ultrasonic wave conducting medium, the most common of which is water. Thus this system is especially useful in flow induced vibration measurements and monitoring of components in the power generation, processing and petrochemical industries, especially when the vibrating frequencies are expected to be low. Thus the system may be used to "non-intrusively" monitor and measure vibration of internal components of all types of valves exactly the same way as is used to measure disc vibrations inside check valves. Providing the casing is not excessively thick and the material is penetratable by ultrasonics, internal components of various pumps including reciprocating and centrifugal pumps can also be monitored using this system and its methodology.

In addition to the enumerated valve vibration monitoring applications described earlier, this system and its is also useful in monitoring the vibration of nuclear reactor internals.

Figure 7:
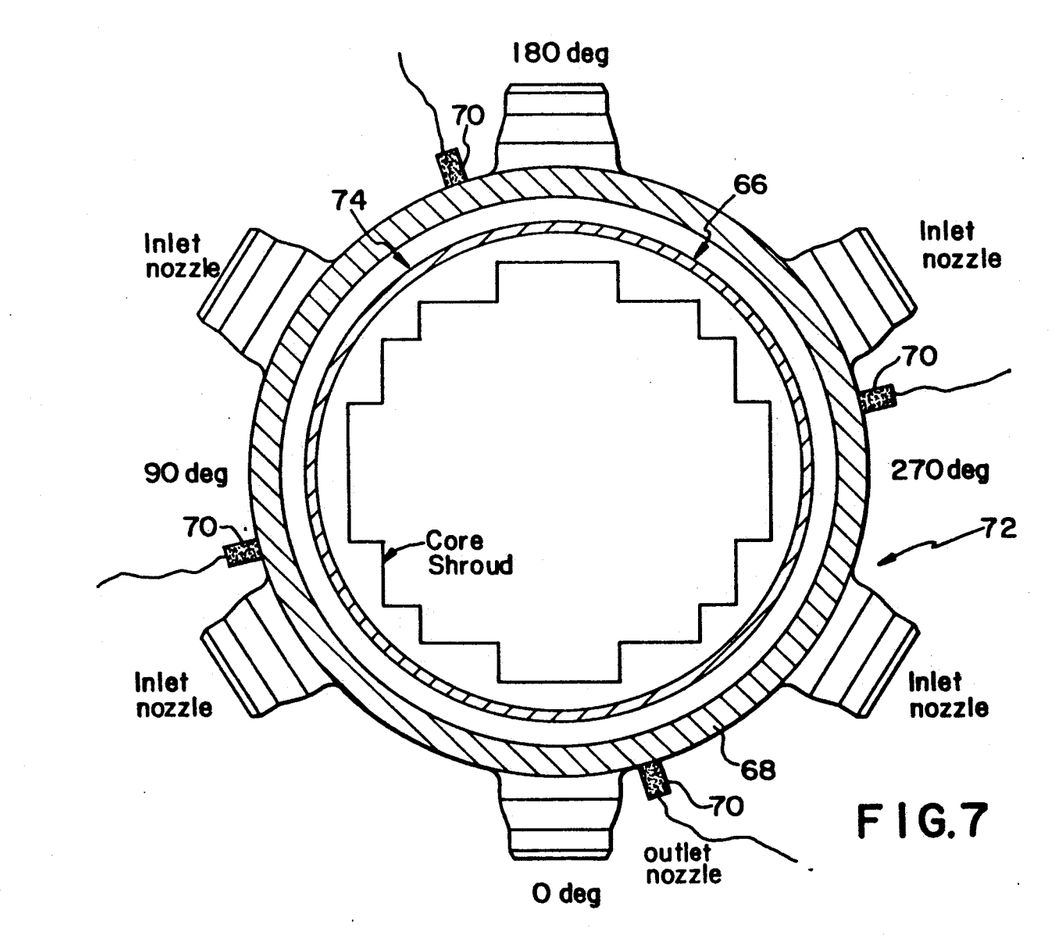
FIG. 7 depicts four ultrasonic transducers mounted on a nuclear reactor to replace four in-core neutron noise detectors normally used to monitor the vibration of the core of the nuclear reactor.

As a safety precaution, the vibration of the core support structure (66) and the thermal shield (68) in commercial pressurized nuclear reactors (PWR) are periodically monitored during normal operation of the plant. Presently, the only practical "non-intrusive" device to measure the vibration characteristics of these internal components is empirically based on study involving the neutron noise signature acquired by ex-core detectors. FIG. 7 shows how four ultrasonic transducers (70) are externally mounted on the reactor vessel (72) to transmit ultrasonic waves through the vessel, the water filled downcomer annulus (74), and reflected back by the core support structure (66), to monitor its vibration characteristics. Similarly components like the plenum cylinder and thermal shield (68) may also be monitored by this method. Radiation-resistant, high-temperature epoxy is used to mount the ultrasonic transducers (70) on the reactor vessel.

The potential of using ultrasonic vibration measuring device to monitor vibration of internal components is even more applicable to the New Production Reactors designed to produce weapon grade Plutonium and Tritium. Because the New Production Reactors has a much lower operating pressure, the reactor vessel is much thinner than that of the PWR, thus making ultrasonic penetration much easier. Because of their thinner walls and larger diameters compared with those in previous PWR, the estimated flow-induced vibration amplitudes of the reactor vessel and the core support cylinder are much larger than their counterparts in previous PWR, thus making it easily measurable by the ultrasonic sensor (70). Because of the much lower operating temperature, there are more adhesives to choose from for mounting the ultrasonic transducers on the reactor vessel to measure the relative vibration amplitudes between the reactor vessel and the core support cylinder. The ultrasonic sensor (70) can also be used for in-service vibration monitoring of many other components in nuclear power reactors in general.

Another application for the described method and system includes the in-service vibration monitoring of heat exchanger internals.

A typical nuclear plant has over 50 heat exchangers, including the steam generator. Flow-induced vibration related problems in these heat exchangers have in the past caused many unscheduled down times. Presently the only method used to monitor flow-induced vibration of heat exchanger internal components is to "listen" from the outside, or at the tube ends if they are accessible, using accelerometers or microphones. This method works only if flow-induced vibration causes rattling and impacts between the internal components. By that time these sounds are "heard" it may be too late and even then, external monitoring is only an indirect way of qualitatively assessing the severity of vibration. Very often even the location of impact cannot be determined precisely. The ultrasonic vibration system and methodology solves these problems. By temporarily mounting the ultrasonic transducer on the outer surface of the heat exchanger shell, the location of impact can be easily determined. It can also be used to measure the vibration frequencies and amplitudes of heat exchanger components such as tubes, tie rods, shrouds or orifice plates, without disassembling the heat exchanger.

In summary, the commercial ultrasonic system and methodology can be used together with modern digital signal analysis techniques as a quantitative vibration measurement instrument. Its application to measure vibration of discs inside check valves have been demonstrated. For this application peak-to-peak vibration amplitudes as small as 0.03-inch had been quantitatively measured. Additionally, there are many other applications as an in-service, non-intrusive flow-induced vibration monitoring system, particularly to monitor components in the power generation, processing and petrochemical industries. In some of these applications, minor modifications to the programming of software for the ultrasonic instrument (50) and the digital filter may be necessary.

Since the ultrasonic instrument (50) has no low frequency limit it thus supplements the audio device (12), which becomes insensitive below 10 Hz. The ultrasonic device (14) is essentially a low-frequency sensor with an upper frequency limit of only a few hundred Hz which can accurately measure vibration amplitudes as small as 0.03-inch, and it works if the vibrating component is immersed in an ultrasonic conducting medium such as water. However, the acoustic device covers the limitations of the ultrasonic device (14) to make the combined system (10) a powerful monitoring system.

It will be understood that certain modifications and details have been deleted for the sake of conciseness and readability but that such are intended to be covered by the following claims.

I claim:

1. A method of ultrasonically measuring on a quantitative basis the vibration of a vibrating internal part known to have a low frequency vibration inside a device containing an ultrasonic conducting medium comprising:
   mounting an ultrasonic transducer and receiver on a face of said device to be aligned with said vibrating internal part, wherein said ultrasonic transducer emits a series of pulses having pulse rate at least two times higher than a vibration frequency of the vibrating part.

2. A method of ultrasonically measuring as set forth in claim 1, wherein said ultrasonic transducer also acts as an ultrasonic receiver to receive said ultrasonic pulse reflected from said vibrating part and wherein said ultrasonic transducer emits no pulses while receiving said reflected pulses.

3. A method of ultrasonically measuring as set forth in claim 1, wherein said pulse rate is no higher than 1,000 per second.

4. A method of ultrasonically measuring as set forth in claim 1, wherein said digital filtering further includes the step of enlarging a local area of the recording and displaying same to allow the determination of the amplitude and frequency of the vibration of the vibrating part.

5. A method of ultrasonically measuring as set forth in claim 1, wherein said recording is done by a digital recorder on digital audio tape by in-situ instruments located within the area of the device and wherein said digital filtering is done on the digital audio tape, ex-situ from the device at a computer station to provide an analog display on a screen of the computer station.

6. A method of ultrasonically measuring as set forth in claim 1, wherein the device is a check valve having an ultrasonic transducer mounted on a face of the check valve to be aligned with a vibrating disc within the check valve.

7. A method of ultrasonically measuring as set forth in claim 6, further including an acoustic measurement of qualitative conditions of elements inside the check valve and recording of the acoustic measurement on a cross-correlated basis with the ultrasonic pulse recording.

8. A system for quantitatively monitoring the vibration of a valve element movably located within a valve body comprising:
   pulse generator means for sequentially generating ultrasonic pulses and for receiving reflected ultrasonic pulses and establishing signals indicative thereof;
   ultrasonic transducer means mounted on the valve body to face the vibrating valve element for emitting ultrasonic pulses to the vibrating valve element;
   recording means connected to said pulse generator means for recording the signals established by said pulse generator means;
   digital signal analysis means for providing a display of vibration of the valve element from which a quantitative analysis may be made including digital filtering of said signals from said pulse generator; and
   wherein said digital signal analysis means includes a PC based digital filter for filtering said pulse generator signals and displaying same on a high resolution screen of said PC to allow a quantitative analysis of said signals from said pulse generator and a quantitative analysis of said valve element vibration thereby.

9. A system as set forth in claim 8, further including acoustic means for providing an auditory record of the valve internal element vibrations.

10. A system as set forth in claim 9, wherein said acoustic means includes an accelerometer mounted on the valve body to qualitatively measure the vibration of the valve internal element inside the valve body.

11. A system as set forth in claim 10, wherein said accelerometer is connected to said recording means to allow a cross-correlated analysis of both the ultrasonic transducer means and said accelerometer.

12. A system as set forth in claim 11, wherein the output of said recording means is connected to a digital recorder to provide a record of the recording on digital audio tape.

13. A system for quantitatively monitoring the condition of a movable element within a body enclosing said movable element in an ultrasonic pulse conducting fluid medium comprising:
   ultrasonic transducer means mounted on said body to selectively send to said movable element and receive reflected therefrom ultrasonic pulses;
   means for recording a time record of said pulses being selectively sent and received from said movable element;
   PC based digital filtering means for filtering the time record of said recording means to provide a visual time display of the position of said movable element; and
   a high resolution PC screen for displaying the time record of said PC screen for displaying the time record of said PC based digital filtering means.

14. A system as set forth in claim 13, further including acoustic means for checking the condition of the movable element within said body.

15. A system as set forth in claim 14, wherein said body is a check valve and said movable element is a pivotable valve disc and said acoustic means includes an accelerometer mounted on an external surface of the check valve body to provide signals indicative of the audible sounds within the body of the check valve.

16. A system as set forth in claim 15, wherein said ultrasonic transducer means includes an ultrasonic transducer mounted on an external surface of said check valve body to send and receive ultrasonic pulses from the pivotable valve disc.

* * * * *